United States Patent [19]

Jones, Jr. et al.

[11] 4,370,602
[45] Jan. 25, 1983

[54] WATERBED VIBRATOR

[76] Inventors: Johnny O. Jones, Jr., #1 Cross Creek, Irvine, Calif. 92714; Charles C. White, Jr., 1300 Adams, Apt. 5P, Costa Mesa, Calif. 92626

[21] Appl. No.: 135,297

[22] Filed: Mar. 31, 1980

Related U.S. Application Data

[62] Division of Ser. No. 800,588, May 25, 1977, abandoned.

[51] Int. Cl.³ .......................................... H02K 33/00
[52] U.S. Cl. ...................................... 318/114; 318/28; 318/130; 128/32; 128/33; 128/41
[58] Field of Search .......................... 128/32, 33, 41; 318/114, 128, 130; 331/47, 106

[56] References Cited

U.S. PATENT DOCUMENTS

| | | | |
|---|---|---|---|
| 3,665,343 | 5/1972 | Thompson | 331/145 |
| 4,054,847 | 10/1977 | Fukaya | 331/145 |
| 4,101,816 | 7/1978 | Shepter | 318/130 |
| 4,105,024 | 8/1978 | Raffel | 128/33 |

*Primary Examiner*—B. Dobeck
*Attorney, Agent, or Firm*—Larson and Taylor

[57] ABSTRACT

A vibrator mechanism, including a transducer and driving circuit, particularly adapted to vibrating a waterbed, includes two independently controlled vibration sources, each of which can generate vibration of varying amplitude and frequency. These two sources are typically mounted at opposite ends of a waterbed frame and vibrated at different frequencies so that interference waves may be produced within the water of the bed to produce a pleasing effect for the user. Additional circuitry is described which provides a time varying frequency and amplitude for each of the vibrators, and this circuitry is in turn controlled by a clock circuit so that, by using the time varying frequency and amplitude, the user may be slowly lulled to sleep or slowly awakened using the vibration within the waterbed as a stimulus for controlling the rate of falling asleep and waking up.

16 Claims, 8 Drawing Figures

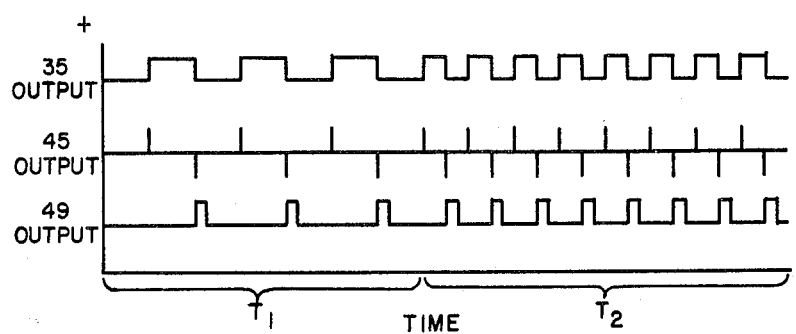
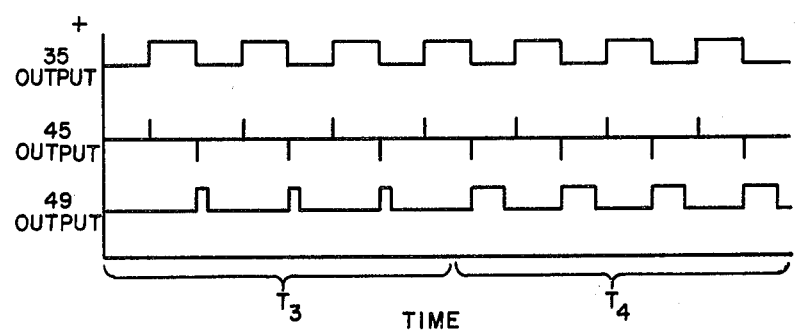
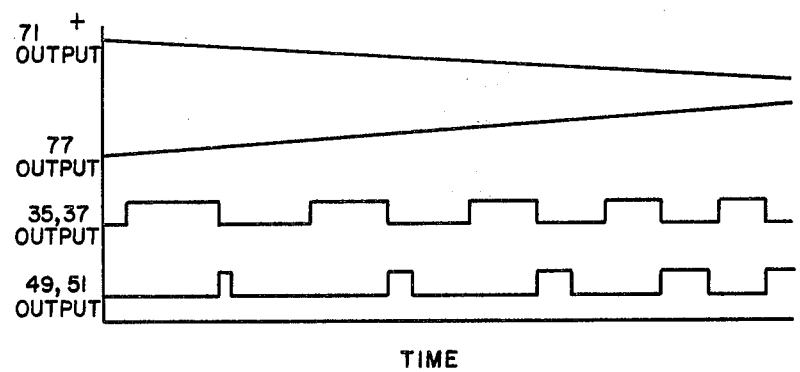
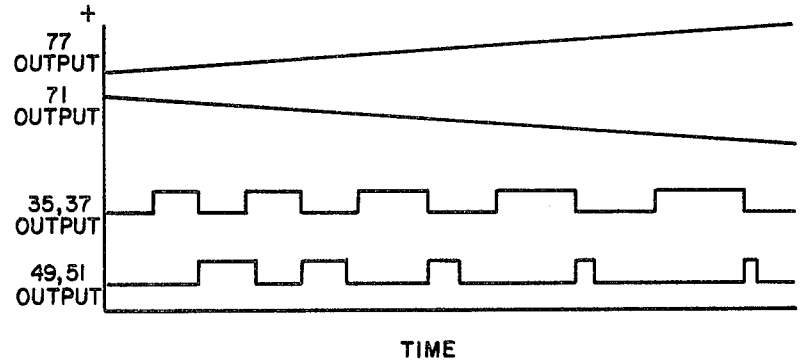

WATERBED VIBRATOR

This is a division of application Ser. No. 800,588, filed May 25, 1977, now abandoned.

BACKGROUND OF THE INVENTION

The vibration of articles of furniture for inducing relaxation in the user has been accomplished in the prior art using a variety of mechanisms. Because of the ready availability of high power, 60-cycle current, however, the bulk of these systems have used either a direct 60-cycle transducer to induce vibration or a motor with an eccentric weight operating from the 60-cycle current. In some instances where a motor with an eccentric weight is used, the speed of the motor is variable, for example, using a solid state control or a rheostat. Such devices, however, necessarily control the amplitude and frequency of vibration simultaneously, and it is impossible, without altering the eccentricity of the weight (a difficult operation) to alter the frequency and vibration independently.

In systems where two eccentric weight motors are used on a single piece of furniture, it has been found that interference waves can be produced in the furniture, which waves result in a pleasant sensation for the user. These systems, however, as mentioned above, can produce such interference waves only at predetermined amplitudes depending completely upon the frequency selected for motor operation.

Thus, in the prior art, vibration transducers have typically been limited to operation from the available 60-cycle current and have not been utilized to independently vary the frequency and amplitude of the vibration. Motors used in the prior art are limited in the variation of waves which may be induced and, furthermore, are subject to substantial wear generated by the eccentric weight.

SUMMARY OF THE INVENTION

The present invention alleviates these and other difficulties inherent in prior art furniture vibrator designs by utilizing a solid state driving circuit in conjunction with a vibration transducer to generate vibration in furniture, and particularly in waterbeds, having independently variable amplitude and frequency characteristics. In a particular embodiment of the present invention, two such vibration systems are used so that interference waves may be produced within the furniture of varying amplitude and frequency.

The present invention further provides the ability to induce in the vibration system a time varying amplitude and frequency characteristic which is particularly adaptable for use in combination with an alarm clock circuit for slowly inducing sleep or slowly waking up the user. When this circuit is used in combination with a pair of transducers and vibrators, it is possible to slowly induce sleep or wake the operator up while at the same time producing pleasant interference waves within the furniture by vibrating the pair of transducers at different frequencies.

The ability to independently vary the amplitude and frequency of a vibrator attached to furniture, and particularly to waterbeds, is extremely important in that substantially different effects can be achieved by producing, for example, low frequency, high amplitude waves as opposed to high frequency, low amplitude wave motion within the bed, one of which may induce a very relaxed state in the user whereas the other may heighten the awareness and sensitivity of the user.

These and other features of the present invention are best understood through the following detailed description which references the drawings in which:

FIG. 4 is a schematic illustration of signal levels on various lines of the circuit of FIG. 3, illustrating frequency adjustments;

FIG. 5 is a schematic illustration similar to that of FIG. 4, but illustrating amplitude adjustments;

FIG. 6 is a schematic illustration of signals on other lines of the circuit of FIG. 3, illustrating the alarm operation of the circuit;

FIG. 7 is a schematic illustration similar to that of FIG. 6, but illustrating the sleep inducing operation of the circuit.

DETAILED DESCRIPTION OF THE PREFERRED EMBODIMENT

Figure 1:
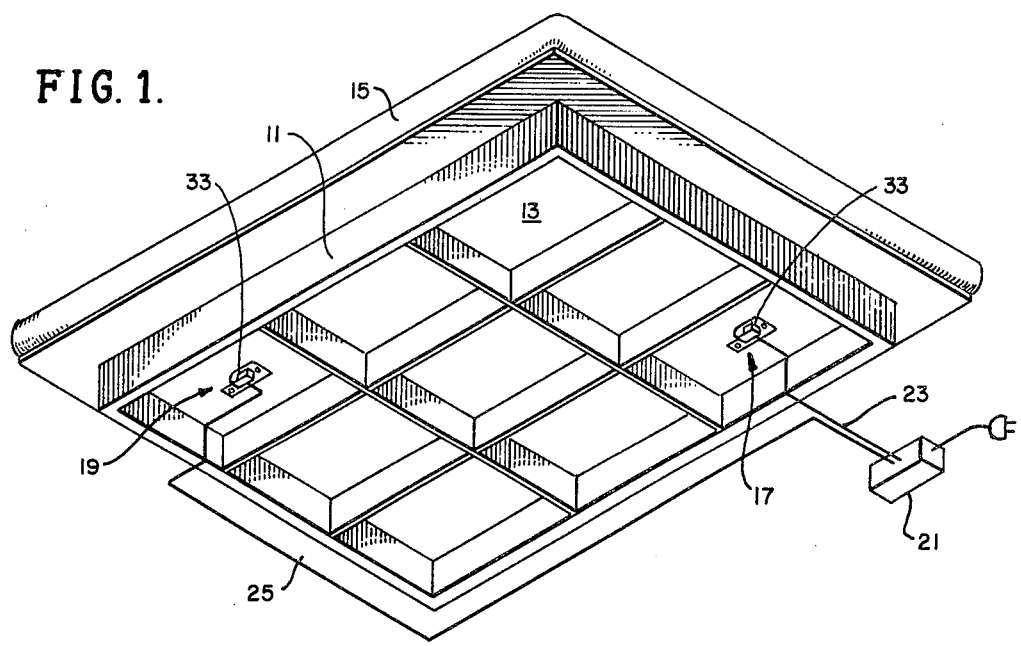
FIG. 1 is a perspective view showing the vibration mechanism of the present invention attached to the underside of a typical waterbed.

Referring initially to FIG. 1, a typical waterbed is shown to include a deck support grid 11, formed of vertical support members, positioned below and supporting a flat, horizontal deck member 13. These elements 11,13 are typically constructed of wood and are used to support a flexible water mattress 15 above the floor. Attached to the underside of the deck 13, preferably at diagonally opposed corners of the deck 13, are a pair of vibration transducers 17,19. Each of the transducers 17,19 is connected electrically to a driving circuit 21 by means of wires 23 and 25, respectively.

The system of the present invention permits each of the transducers 17 and 19 to be independently energized at varying amplitudes and frequencies. When the transducers 17 and 19 are operated at different frequencies, each of these frequencies will be induced in the water of the mattress 15 and will be felt by anyone lying on the mattress 15. In addition, an interference frequency, the difference between the frequencies of the transducers 17 and 19, will form an interference wave within the mattress 15 which can also be felt by the user. This interference wave can typically be of extremely low frequency while, at the same time, each of the transducers is producing a primary, higher frequency. For example, if the transducer 17 is vibrating at 45 cycles per second and the transducer 19 at 42 cycles per second, they will produce an interference wave of 3 cycles per second. This low frequency interference wave can be extremely soothing to the user and can produce an altogether different sensation from that produced by the direct vibration of either of the transducers 17,19 alone.

Figure 2:
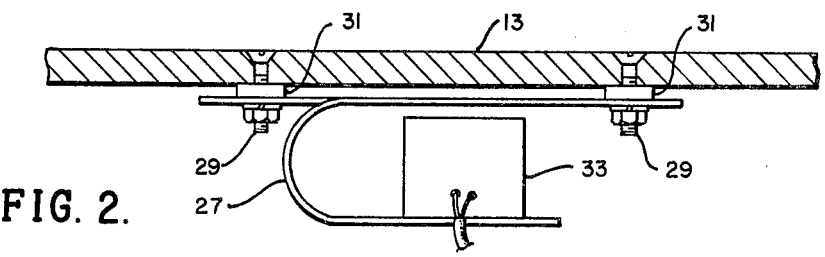
FIG. 2 is an elevation view of the vibration transducer utilized in the system shown in FIG. 1.

Referring now to FIG. 2, the particular transducer utilized in the system of FIG. 1 will be described. As previously stated, the transducer 17 is connected to the deck 13. In the preferred embodiment, it includes a generally u-shaped band of spring steel 27, one flat side of which is connected, as by plural screws 29, to the deck 13. The band 27 is preferably isolated from the deck 15 by washers 31. The opposite flat side of the u-shaped band 27 mounts a magnet coil 33. This coil, when energized, will attract the opposite flat side of the u-shaped spring steel band 27. Thus, when the magnet coil 33 is induced with a cyclical current, it will vibrate, so that the free side of the u-shaped spring steel band 27 is forced to oscillate relative the stationary side. Since the magnet 33 is relatively heavy, this vibration will, in turn, induce vibration in the deck 13 and in the mattress 15 above the deck. The transducer 17 is capable of vibrating at a variety of frequencies, depending upon the inducing current, and the amplitude of vibration can be varied by altering the level of the inducing current, as will be described in detail below.

Figure 3:
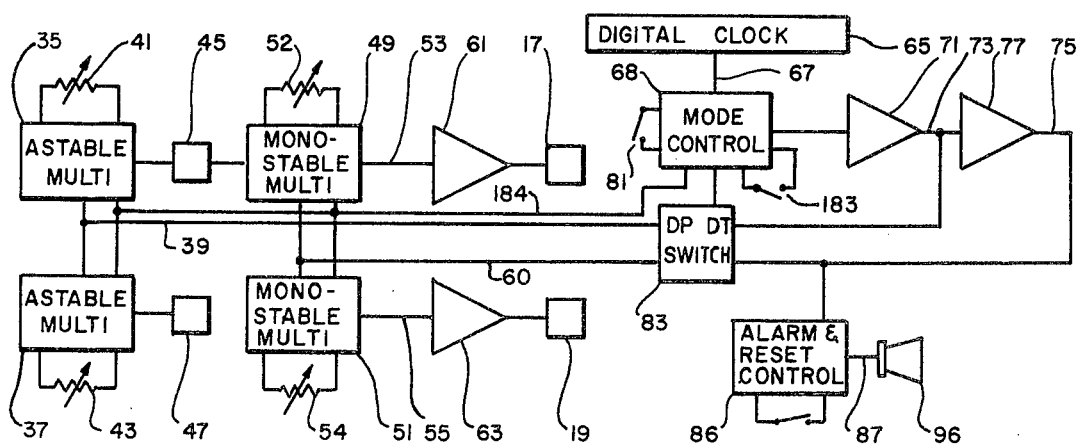
FIG. 3 is a block diagram illustration of the circuitry used for driving the transducers of FIG. 2.

Referring now to FIG. 3, the transducers 17 and 19 are shown together with the control circuit which forms the driving circuit 21 of FIG. 1. This circuit includes a pair of astable multivibrators 35 and 37 are shown connected to a control line 39 which, together with a pair of variable resistors 41 and 43, controls the multivibrator frequency. It will be understood that each of the astable multivibrators 35,37 produces an output square wave, the frequency of which is determined by the setting of the variable resistors 41,43 or the voltage on the control line 39.

The output of each of the astable multivibrators 35,37 is conducted by means of a pulse shaping circuit 45,47, respectively, to a pair of monostable multivibrators 49,51. The monostable multivibrators are responsive to the output frequency signal from astable multivibrators 35,37 to produce a controlled duration output pulse for each negative going input pulse from the pulse shape circuits 45,47 so that, on their output lines 53,55, respectively, the multivibrators 49,51 each produce a signal, the frequency of which is determined by the astable multivibrators 35,37 and the pulse width of which is determined by the monostable multivibrators 49,51. This pulse width ultimately determines the amplitude of vibration produced by the system. In a manner similar to the resistors 41,43, variable resistors 52,54 control the time delay of the monostable multivibrators 49 and 51, respectively. Additionally, this time delay may be set by a control signal on line 60.

Referring briefly to FIG. 4, the output of astable multivibrator 35 is shown as a function of time and, for purposes of illustration, is shown as having a first relatively low frequency during a time period $T_1$ and a second relatively high frequency during a time period $T_2$. Corresponding with this output, the output of the pulse shape circuit 45 is shown, as is the output of monostable multivibrator 49.

In this example, the pulse width of the monostable multivibrator 49 is left unchanged as the frequency of the astable multivibrator 35 changes. It can be seen that the frequency at the output of the monostable multivibrator 49 changes significantly between times $T_1$ and $T_2$, but the pulse width does not appreciably change.

In the illustration of FIG. 5, times $T_3$ and $T_4$ are shown and the outputs of elements 35, 45, and 49 are again depicted. In this example, however, the setting of the astable multivibrator 35 is left unchanged, so that the frequency remains constant. During the time $T_3$, the monostable multivibrator 49 is set for a relatively short time delay, so that the amplitude of vibration will be relatively small. During the time $T_4$, however, the monostable multivibrator 49 has an increased time delay, so that the output pulse width, and the resulting amplitude of vibration, is substantially increased without altering the output frequency.

From the diagrams of FIGS. 4 and 5 it can be seen that any combination of output frequency and amplitude which is desired may be achieved by independently varying the resistors 41 and 43 for frequency adjustment, and the resistors 52 and 54 for amplitude of vibration adjustment.

Referring once again to FIG. 3, the output signals on lines 53 and 55 are coupled to driver amplifiers 61 and 63, respectively, which are in turn connected to drive the transducers 17,19 in accordance with the signals on lines 53,55.

While the frequency and amplitude of vibration may be controlled as previously described using the variable resistors 41, 43, 52, and 54, the present invention includes an alternate control responsive to a digital clock circuit 65. This clock circuit produces an alarm signal on line 67 in typical fashion, which is used to drive a mode control circuit 68 at the time for which the alarm of the digital clock 65 is set. Once it is set, the mode control 68 drives an integrator 71 which produces a negative-going ramp signal on line 73. An inverted, positive-going ramp signal is produced on line 75 by an inverting amplifier 77 in response to the signal on line 73.

The mode control 68 includes, as a second input, a sleep switch 81 which is closed by the operator to place the circuit 21 in a sleep inducing mode. Either of the inputs, 81,67, will initiate control signals from the mode control 68 to enable the integrator 71. In addition, however, the mode control operates a double pole, double throw switch 83 in accordance with the initiating signal 67,81. Thus, the mode control 68 controls the switch 83 to connect line 39 to line 73 and line 60 to line 75 during the alarm period (line 67 signal) or, alternatively, line 60 to line 73 and line 39 to line 75 during the sleep inducing period (switch 81).

In addition, the mode control 68 automatically produces a signal on a line 184 which enables the multivibrators 35,37,49,51 during the alarm and sleep inducing modes. A switch 183 is also provided for manually enabling the multivibrators 35,37,49,51.

The output of the inverting amplifier 77 and mode control 68 are additionally connected to an alarm and reset control 86 which monitors the output voltage on line 75 and provides an output signal on a line 87 when the alarm ramp signal has terminated. This signal on line 87 drives a speaker 96 to give an audible alarm sound indicating that the alarm cycle is completed. The speaker 96 assures that the operator wakes up.

Referring to FIGS. 6 and 7, the integrator 71 ramp signal, inverter 77 ramp signal, and the control of the multivibrators 35, 37, 49, and 51 in response to these signals will be described. FIG. 6 shows the alarm sequence, that is, the sequence normally utilized in the morning to slowly wake the operator prior to the energization of the audio speaker 96. It will be seen that, during a predetermined time period, the output of the integrator 71 is a linearly decreasing ramp signal while the output of the inverting amplifier 77 is a linearly increasing ramp signal. The rates of change of these signals in FIGS. 6 and 7 are greatly exaggerated to ease understanding, the transitions actually occurring over an extended period of time, for example, ½ hour.

The multivibrators 35 and 37 respond to the ramp signal from the integrator 71 by producing an output frequency which increases linearly with time. The multivibrators 49 and 51 simultaneously respond to the output from the inverting amplifier 77 by producing a linearly increasing amplitude signal. Thus, during this alarm period, both the frequency and the amplitude of vibration are linearly increased until they reach the levels preset by resistors 41, 43, 52, and 54. This increasing frequency and amplitude slowly brings the user from a subconscious sleep level to a level of heightened awareness, at the end of which the alarm 96 sounds, finally waking the operator.

As shown in FIG. 7, when the sleep switch 81 is closed, the output of the integrator 71 and the inverting amplifiers 77 are identical to that shown in FIG. 6. In this case, however, the interconnections are reversed by the double pole, double throw switch 83, so that the integrator 71 controls the multivibrators 49 and 51 and the inverting amplifier 77 controls the multivibrators 35 and 37. The result of this switching is that the frequency as well as the amplitude of the output signal from the monostable multivibrators 49,51 are reduced from the value preset by resistors 41, 43, 52, and 54 to a very low frequency, low amplitude level, slowly bringing the operator from a level of heightened awareness to a level of relatively deep sleep.

It will be seen that by altering the values of resistors 41 and 43, interference waves can be generated during the sleep and alarm phases of operation as may be desired. The present circuit thus permits a very unique system for producing time variations in the frequency and amplitude of vibration to lull the user to sleep or to slowly waken him as desired.

Figure 8:
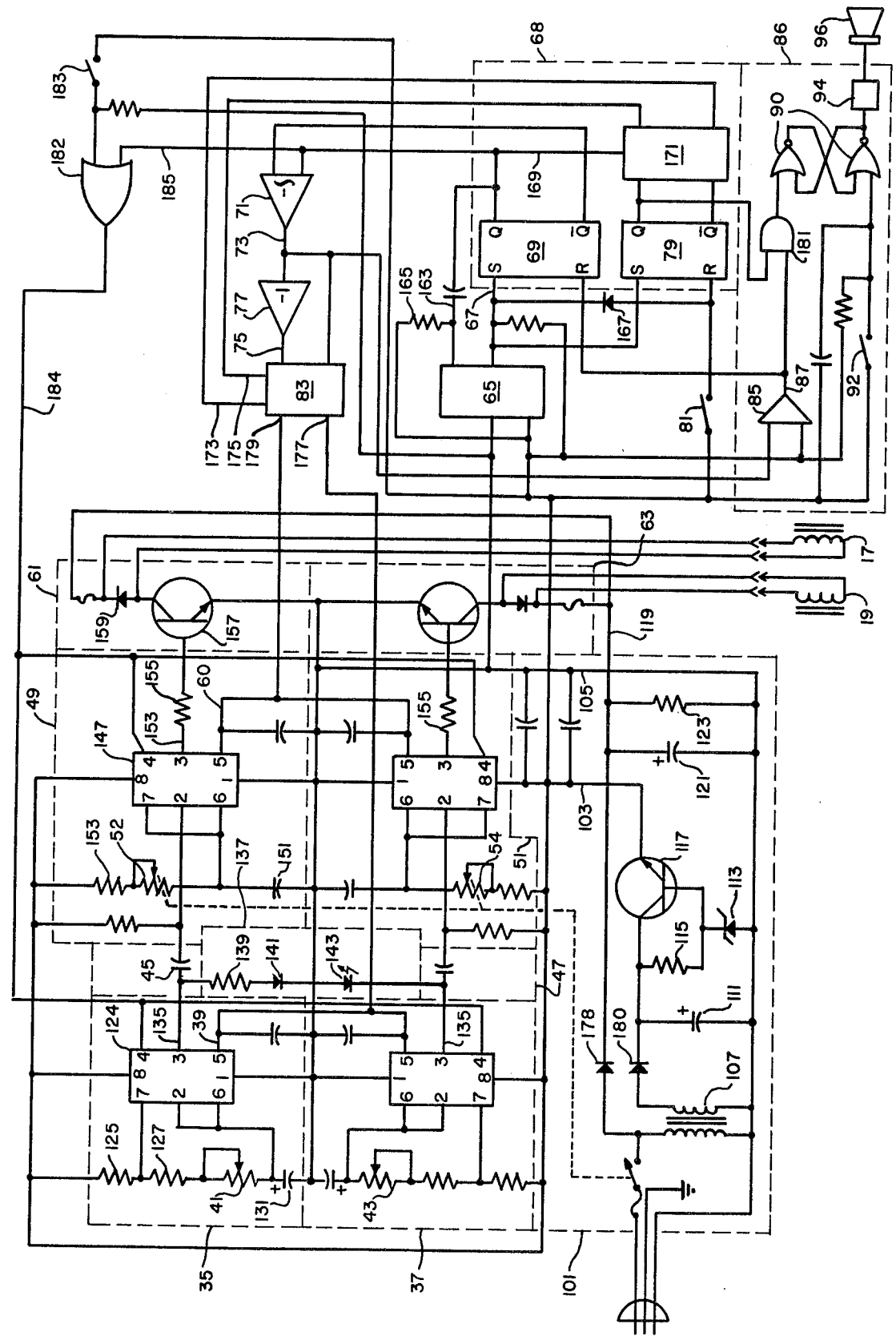
FIG. 8 is a detailed circuit diagram showing the circuits which make up the black box members of FIG. 3.

Referring now to FIG. 8, the detailed circuitry, represented in block form in FIG. 3, will be described.

A power supply 101 supplies a V+ voltage on output line 103 which is referenced to an output neutral or ground line 105. This voltage is produced by a stepping transformer 107, the secondary of which is connected in series with a filtering capacitor 111 and rectifying diode 180, which is used, together with resistor 115 and reference diode 113 for controlling a regulating transistor 117 to provide the desired voltage. In addition, the power supply 101 provides filtered driving current for the vibrators 17,19 by connecting a capacitor 121 and rectifying diode 178 in series with the 60-cycle source. A pair of output lines 105,119 are connected in shunt with the filter capacitor 121 and a bleeder resistor 123.

The astable multivibrators 35 and 37 are identical in construction and thus only the multivibrator 35 will be described. This multivibrator uses an integrated circuit 124 commonly available in the art under standardized part number NE555 (or others). Pin 8 of this integrated circuit is connected to line 103 and pin 1 thereof is connected to line 105 for powering the integrated circuit. Fixed resistors 125 and 127, along with variable resistor 41 and capacitor 131, all connected in series between lines 103 and 105, are connected at their junctions to pins 2, 6, and 7 of the integrated circuit 124. These components 125, 127, 41, and 131 control the frequency of the astable multivibrator configured integrated circuit 124 in the absence of a voltage control signal on pin 5.

Pin 4 of the integrated circuit 124 is connected to line 184 for enabling (when a signal is present on line 184) or disabling (when no signal is present) the integrated circuit 124.

Line 39, previously mentioned, is connected to pin 5 of the astable multivibrator 124 and will alter the bias on pins 2, 6, and 7 to set the free running frequency of the multivibrator 124 when a voltage is present. As the voltage on line 39 increases, the frequency of the integrated circuit 124 will decrease.

As previously mentioned, the output at pin 3, line 135, is a square wave, the frequency of which is controlled by the variable resistor 41 or the voltage on line 35, is the latter is above ground level, that is, the level on line 105.

Each of the output lines 135 of the multivibrators 35 and 37 are connected to a balance indicator light 137, comprising a resistor 139, diode 141, and light emitting diode 143 connected in series between these outputs. The light emitting diode 143 is mounted on the front panel of the circuit chassis and is illuminated to show maximum intensity in a cyclicly changing pattern, the frequency of which is equal to the difference frequency between the astable multivibrators 35 and 37. As previously mentioned, this difference in frequency is the interference wave frequency within the waterbed and the light emitting diode 143 makes it easy for the user to adjust the frequencies of the multivibrators 35 and 37 to provide a desired difference frequency.

The outputs of each of the astable multivibrators on lines 135 are additionally connected to the inputs of the monostable multivibrators 49 and 51. These multivibrators are also identical in construction, thus only multivibrator 49 will be described. This multivibrator is also built around an NE555 integrated circuit 147, including pin 8, connected to line 103 and pin 1 connected to line 105 for supplying power to the circuit. The output on line 135 from the astable multivibrator 35 is connected to the input at pin 2 of the integrated circuit 147 through a pulse shaping capacitor 45. The capacitor 45 produces negative going pulses at the trailing edge of the output square wave on line 135 for triggering the multivibrator 49. The input on pin 2 of the integrated circuit 147 is responsive only to the negative going pulses, such that the frequency of the integrated circuit 147, but not its pulse duration, is identical to the frequency of the signal on line 135.

Pins 6 and 7 of the integrated circuit 147 are each connected at the junction of the variable resistor 52 and capacitor 151 which are, in turn, connected in series with a fixed resistor 153 between the V+ line 103 and ground 105. The variable resistor 52 sets the pulse duration of the monostable multivibrator 49 and thus the intensity of vibration caused by the waterbed vibrator. It can be seen, therefore, that the resistor 52, in setting the pulse duration, changes the vibration amplitude independent of the frequency, which is determined by the resistor 41 or the signal on line 39.

A voltage control signal on line 60 is connected to pin 5 of the integrated circuit 147 and alters the pulse duration signal at pin 6, if it is enabled. As the voltage on line 60 increases, the pulse width of the monostable multivibrator 49 increases, that is, the time period during which the output voltage is high is increased. The output at pin 3, line 153, is thus a rectangular wave, the frequency of which is determined by the astable multivibrator integrated circuit 124 and the pulse duration of which is determined by the monostable multivibrator integrated circuit 147. As with the astable multivibrator, a signal supplied to pin 4 from line 184 enables or disables the monostable multivibrator 49.

The outputs of the monostable multivibrators 49 and 51 are connected through bias resistors 155 to driver amplifiers 61 and 63. These amplifiers are identical in construction and only the amplifier 61 will be described. The amplifier 61 includes a transistor 157 which is operated as a switch, that is, either totally cut off or saturated. When the output on line 153 is at ground level, the transistor 157 is cut off. When the output on line 153 is high, the transistor 157 is saturated and thus conductive. When conductive, the voltage on lines 119 and 105 appears across the vibrator or transducer 17 and the current through the vibrator 17 increases until limited by the resistance of the vibrator. When the transistor 157 cuts off, the inductance of the vibrator 17 is prohibited from damaging the transistor 157 by a shunting diode 159 in typical fashion. The vibrator 19 is operated in an identical fashion from the driver amplifier 63.

Turning now to the control circuitry used for operating this vibrator circuit, a digital clock 65, in the form of an integrated circuit chip, readily available on the market, is supplied with operating voltages from lines 103 and 105 and provides, at a time set by the operator, an alarm signal on line 67. An alarm reset input on line 163 responds to negative going pulse signals to reset the alarm circuit of the clock 65. The line 163 is normally clamped through a resistor 165 to the voltage on line 103.

Signals on the line 67, indicating that the alarm time has been reached, set a pair of flip-flops 69 and 79 which form a part of the mode control 68. A diode 167 prevents the signal from attempting to both set and reset the flip-flop 79 at the same time. The flip-flop 69 is used to cycle the vibrators, whereas the flip-flop 79 determines the direction of cycling, that is, whether the vibrator circuit is being used to induce sleep in the operator or to wake the operator up slowly. When the flip-flop 79 is set by the signal on line 67, the set state indicates a wake up phase. Alternatively, when the flip-flop 79 is reset by a manual closure of the switch 81, the sleep switch, the sleep inducing cycle of the vibrator will begin. Note that a diode 167 sets the flip-flop 69 in response to the switch 81 so that the flip-flop 69 is set for either the sleep or wake up mode. The output of the flip-flop 69 is connected to the integrator 71, the output of which is at ground potential until the flip-flop 69 is set. At that time the output on line 73 changes linearly from a high potential, the potential on line 103, to ground level, the potential on line 105. The inverting amplifier output is opposite that of the integrator 71, that is, when the flip-flop 69 is set, the output on line 75 changes linearly from ground potential, the potential of line 105, to a positive voltage potential, that of line 103. Each of these outputs on lines 73 and 75 are applied to the double pole, double throw solid state switch 83, a commonly available integrated circuit.

When the flip-flop 79 is set by the alarm on line 67, and when the flip-flop 69 is set, a signal on line 169 will close a double pole, single throw solid state switch 171 to conduct the set voltages from the Q and $\overline{Q}$ outputs from the flip-flop 79 to the switch control inputs of the double pole, double throw integrated circuit switch 83. Alternatively, when the sleep switch 81 has been closed so that the flip-flop 79 is reset, but the flip-flop 69 is set, the signal on line 169 will close the double pole, single throw solid state switch 171 to connect the reset voltages from the Q and $\overline{Q}$ outputs of the flip-flop 79 to the switch 83. The double pole, double throw integrated switch 83 is controlled by the outputs from switch 171 on lines 173 and 175, such that if the flip-flop 79 is set, indicating a wake up sequence, the negative going ramp signal from the integrator 71 will be connected to output 177 of the switch 83, line 39, for controlling the astable multivibrators. At the same time, the positive going ramp signal on line 75 will be connected at output 179, line 60, of the switch 83 for controlling the monostable multivibrators. Alternatively, when the flip-flop 79 is reset indicating a sleep inducing phase, the output of the integrator 71 will be conducted by the switch 83 to the monostable multivibrator on line 60, whereas the output of the inverting amplifier 77 will be connected to the astable multivibrators on line 39. The state of the flip-flop 79 in conjunction with the switch 83 thus conducts the output of the integrator 71 and inverting amplifier 77 to the multivibrators so that the astable multivibrator and the monostable multivibrator in each half of the driving circuit receive a ramp signal going in opposite directions. During the wake up phase the vibrators begin at low frequency, low amplitude and cycle slowly to high frequency, high amplitude. This operation is reversed when flip-flop 79 is reset, that is, the vibrators begin at high frequency, high intensity and cycle slowly to low frequency, low intensity.

When the end of the cycle is reached, flip-flop 69 is reset by a signal produced by the alarm reset and control circuit 86. Specifically, a comparator 85 produces an output voltage signal when the negative going ramp signal from the integrator 71 reaches the level of voltage on line 105. The output 87 of this comparator 85 is ANDed with the Q output of the flip-flop 79 (indicating wake up rather than sleep phase) in an AND gate 181, enabling a gate circuit 90 to energize an audio oscillator 94. A reset switch 92 resets the gate 90, when closed by the operator, to disable the audio oscillator 94. The oscillator is in turn connected to speaker 96 to awaken the user. Also, upon resetting flip-flop 69, line 169 opens the switch 171, which in turn opens the switch 83, thereby removing all control voltages from lines 39 and 60. In addition, line 169 disables a gate 182 (if switch 183 is open). The gate 182 then produces a signal on line 184 to disable all multivibrators 35,37,49,51. If the operator wishes to manually turn on the vibrator system without using the alarm circuit, he closes switch 183, which enables the gate 182 to produce a signal on line 184, enabling multivibrators 35,37, 49,51 regardless of the state of the flip-flop 69.

From the foregoing description, it can be seen that the present circuit, in addition to permitting totally flexible control of both amplitude and frequency of a pair of vibrators adapted for connection to a piece of furniture such as a waterbed, will slowly phase the amplitude and frequency to produce a wake up and sleep mode. During the wake up mode, the amplitude and frequency start at low levels and are gradually increased to heighten the awareness of the individual before an audible alarm sounds. During the sleep phase, the frequency and amplitude begin at a high level and are slowly reduced to induce a restful state in the user.

What is claimed is:

1. A vibrator system for inducing vibration in furniture, comprising:
    a pair of electrical-mechanical transducers mounted at spaced locations on said furniture, each of said transducers producing output mechanical vibration, the amplitude and frequency of which is independently controlled by the respective amplitude and frequency of a pair of independent electrical driving signals;
    means producing said independent pair of electrical driving signals, said means supplying independent cyclicly varying signals to each of said pair of transducers, said means independently controlling the frequency and amplitude of each of said pair of signals, said means comprising:
- a pair of astable multivibrators;
- a pair of monostable multivibrators, each of said monostable multivibrators responsive to one of said astable multivibrators and connected to drive one of said transducers;
- a pair of switching transistors, each of said transistors responsive to one of said monostable multivibrators for controlling the current to one of said transducers; and
- each of said pair of astable multivibrators and each of said pair of monostable multivibrators including an independent control element permitting control of the frequency and amplitude of vibration of said transducers; and
- means producing an output ramp signal for controlling said independent control elements of each of said two astable multivibrators and each of said two monostable multivibrators.

2. A vibrator for inducing vibration in furniture, comprising:
- means responsive to cylic driving electrical current for inducing mechanical vibration in said furniture; and
- means producing said cylic driving electrical current, said driving current producing means comprises means for automatically changing said driving current with respect to time over a predetermined period of time longer than the period of said current to alter said mechanical vibration over said period of time.

3. A vibrator for inducing vibration in furniture as defined in claim 2 wherein said means producing said driving electrical current comprises:
- a multivibrator responsive to a time-varying control signal for continuously changing the time delay of said multivibrator; and means for producing said time-varying control signal.

4. A vibrator for inducing vibration in furniture as defined in claim 3 wherein said control signal producing means comprises means for generating a linear ramp signal.

5. A vibrator for inducing vibration in furniture as defined in claim 2 wherein said means producing said driving electrical current comprises:
- an astable multivibrator automatically changing output frequency over said period of time; and
- a monostable multivibrator responsive to the output signal of said astable multivibrator, said monostable multivibrator automatically changing its delay time over said period of time.

6. A vibrator for inducing vibration in furniture as defined in claim 5 wherein said means producing said driving electrical current additionally comprises:
- means producing a linear ramp signal for controlling each of said astable and monostable multivibrators.

7. A vibrator for inducing vibration in furniture as defined in claim 2 wherein said driving electrical current is cyclical and wherein said period of time is long in comparison with the period of said cyclical current.

8. A vibrator for inducing vibration in furniture as defined in claim 2 wherein both the amplitude and frequency of said mechanical vibration is automatically changed by said means producing said driving electrical current.

9. A vibrator for inducing vibration in furniture as defined in claim 2 wherein said means for producing said driving electrical current comprises means for modulating the amplitude of said driving electrical current.

10. A vibrator for inducing vibration in furniture as defined in claim 9 wherein said means for modulating the amplitude of said driving electrical current comprises means for superimposing a time varying signal upon said driving electrical current.

11. A vibrator for inducing vibration in furniture as defined in claim 2 wherein said means for producing said driving electrical current comprises means for modulating the frequency of said driving electrical current.

12. A vibrator for inducing vibration in furniture comprising:
- an electrical-mechanical transducer mounted on said furniture, said transducer producing output mechanical vibration the amplitude and frequency of which is controlled by an electrical driving signal; and
- means for producing said electrical driving signal, said driving signal producing means comprising means for automatically, and gradually altering said electrical driving signal with respect to time over a predetermined period of time longer than the period of said signal to gradually change said mechanical vibration over said period of time.

13. A vibrator for inducing vibration in furniture as defined in claim 12 wherein said means producing said electrical driving signal gradually increases the frequency and amplitude of said mechanical vibration simultaneously.

14. A vibrator for inducing vibration in furniture as defined in claim 12 wherein said means producing said electrical driving signal gradually decreases the frequency and amplitude of said mechanical vibration simultaneously.

15. A vibrator for inducing vibration in furniture as defined in claim 12 wherein said means producing said electrical driving signal comprises:
- a first multivibrator the delay of which is responsive to an input control signal; and
- a ramp signal generator for producing said control signal.

16. A vibrator for inducing vibration in furniture as defined in claim 15 wherein said first multivibrator is astable and wherein said means producing said electrical driving signal additionally comprises:
- a second monostable multivibrator driven by said first multivibrator, said second monostable multivibrator having a time delay which changes in response to said control signal.

* * * * *